(12) United States Patent
Shioyama et al.

(10) Patent No.: US 10,633,709 B2
(45) Date of Patent: Apr. 28, 2020

(54) METHOD AND APPARATUS FOR DIAGNOSING A TUMOR USING A HISTOGRAM AND EXCLUDING ABNORMAL FLUORESCENCE CORRESPONDING TO DNA ANEUPLOIDY

(71) Applicant: NIHON KOHDEN CORPORATION, Shinjuku-ku, Tokyo (JP)

(72) Inventors: Takahiro Shioyama, Tokyo (JP); Akane Suzuki, Tokyo (JP); Yoshitaka Amano, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 251 days.

(21) Appl. No.: 15/491,327

(22) Filed: Apr. 19, 2017

(65) Prior Publication Data

US 2017/0306412 A1   Oct. 26, 2017

(30) Foreign Application Priority Data

Apr. 26, 2016  (JP) ................. 2016-087586

(51) Int. Cl.
| | |
|---|---|
| C12Q 1/6886 | (2018.01) |
| G01N 21/64 | (2006.01) |
| G01N 15/14 | (2006.01) |
| G01N 15/10 | (2006.01) |

(52) U.S. Cl.
CPC ....... *C12Q 1/6886* (2013.01); *G01N 15/1459* (2013.01); *G01N 21/6428* (2013.01); *G01N 21/6486* (2013.01); *G01N 15/1429* (2013.01); *G01N 2015/1006* (2013.01); *G01N 2015/1486* (2013.01); *G01N 2015/1488* (2013.01); *G01N 2021/6439* (2013.01)

(58) Field of Classification Search
None
See application file for complete search history.

(56) References Cited

U.S. PATENT DOCUMENTS

| 5,633,945 A | 5/1997 | Kamentsky |
| 2008/0108103 A1 | 5/2008 | Ishisaka et al. |
| 2012/0052491 A1 | 3/2012 | Shioyama et al. |
| 2013/0280729 A1 | 10/2013 | Ebi et al. |
| 2014/0030728 A1 | 1/2014 | Shioyama et al. |

FOREIGN PATENT DOCUMENTS

| JP | H10-508690 A | 8/1998 |
| JP | 2012-047594 | 3/2012 |
| JP | 2013-213690 A | 10/2013 |
| JP | 2014-023439 A | 2/2014 |
| WO | 2006-103920 A1 | 10/2006 |

OTHER PUBLICATIONS

European Office action issued in Patent Application No. EP 17 167 028.4 dated Jun. 19, 2018.
Shankey, T. Vincent, et al., "Guidelines for Implementation of Clinical DNA Cytometry" Cytometry, Jan. 1, 1993, pp. 472-477, http://onlinelibrary.wiley.com/store/10.1002/cyto.99014503_ftp.pdf?v=1&t=j6rlf72e&s=f77226a0184623031c47afce425bcdc37686cf25.
Baldetorp, Bo, et al., "Different Calculation Methods for Flow Cytometric S-Phase Fraction: Prognostic Implications in Breast Cancer?", Cytometry, vol. 33, No. 4, Dec. 1, 1998, pp. 385-393.
Bagwell, C. Bruce, "DNA Histogram Debris Theory and Compensation", Cytometry, vol. 12, No. 2, Jan. 1, 1991, pp. 107-118.
Dean, Phillip N., "Data Processing", Flow Cytometry and Sorting, Wiley-Liss, United States, Jan. 1, 1990, pp. 415-444.
Extended European Search Report issued in Patent Application No. EP 17 16 7028 dated Sep. 6, 2017.
Japanese Office action issued in Japanese Patent Application No. 2016-087586 dated Dec. 4, 2019.

*Primary Examiner* — G Steven Vanni
(74) *Attorney, Agent, or Firm* — Pearne & Gordon LLP

(57) ABSTRACT

An apparatus and a method for diagnosing a tumor are provided. A histogram generating section generates a histogram from a result of a measurement of fluorescence intensity of a suspension produced from a target sample. The histogram indicates a relation between the fluorescence intensity and the number of cells. A determination section detects an S phase fluorescence intensity range corresponding to S phase cells based on the fluorescence intensity corresponding to a peak of the number of cells in the histogram, detects an abnormal fluorescence intensity range corresponding to tumor cells, based on a change in the number of cells in the S phase fluorescence intensity range, and performs a diagnosis of a tumor in the target sample based on an index of the number of cells in a range defined by excluding the abnormal fluorescence intensity range from the S phase fluorescence intensity range.

8 Claims, 6 Drawing Sheets

METHOD AND APPARATUS FOR DIAGNOSING A TUMOR USING A HISTOGRAM AND EXCLUDING ABNORMAL FLUORESCENCE CORRESPONDING TO DNA ANEUPLOIDY

CROSS-REFERENCE TO RELATED APPLICATION

The present application claims priority from Japanese Patent Application No. 2016-087586 filed on Apr. 26, 2016, the entire content of which is incorporated herein by reference.

BACKGROUND

The presently disclosed subject matter relates to an apparatus and a method for diagnosing a tumor.

Apparatuses for automatically analyzing cells of a subject and providing information related to malignant alteration of the cells are recently being developed. For example, a related art disclosed in WO2006/103920A1 relates to an apparatus for discriminating cancer and atypical cells based on scattered light acquired by light irradiation on a flow cell in which a measurement sample including cells collected from a subject is caused to flow.

Another related art disclosed in JP2013-213690A relates to an information providing method including detecting a level of progress of a tumor based on an N/C ratio (the ratio of the size of a cell nucleus (N) to the size of a cell (C)) in addition to a DNA amount.

A cell goes through a predetermined cycle (cell cycle) of events including DNA replication, chromosome separation, karyokinesis, cytokinesis, etc., whereby the cell divides itself into two cells, each of which returns to the start point of the cycle. In accordance with stages of the cell, the cell cycle can be divided into four phases, i.e. a G1 phase (preparation and inspection phase for entering an S phase), the S phase (DNA synthesis phase), a G2 phase (preparation and inspection phase for entering an M phase), and the M phase (mitosis phase). The cell cycle may be divided into five phases including a G0 phase (quiescence phase) in addition to the four phases. Cell proliferation is stopped in the G0 phase. Each cell is in a stage corresponding to one of the five phases.

When a cell proliferates in accordance with the cell cycle, chromosomes of a nucleus inside the cell also increase. Therefore, when a DNA amount of the cell is measured, it is possible to evaluate which stage of the cell cycle the cell is in. When a histogram of a number of cells for each DNA amount is generated for a normal body tissue, a highest peak of the number of cells generally corresponds to a G0/G1 phase where the DNA amount is smallest. In addition, a second highest peak in the normal body tissue generally corresponds to a G2/M phase where the DNA amount is largest.

On the other hand, each of cells in which DNA aneuploidy has occurred (i.e. each of cells which may be very likely to be altered malignantly) has a greater number of chromosomes. Therefore, the DNA amount of the cell is also greater. Thus, when a histogram is generated for a body tissue including the malignantly altered cells, a peak different from that for a normal tissue appears on the histogram. An analysis apparatus detects the peak corresponding to the DNA aneuploidy to thereby detect the malignantly altered state.

However, due to the influence of the DNA aneuploidy, the number of cells (a ratio) in the S phase cannot be grasped accurately. For this reason, in some cases, detailed information about the tumor may not be able to be grasped.

SUMMARY

Illustrative aspects of the present invention provide an apparatus and a method for diagnosing a tumor, which can grasp a particular type of a tumor even when there are cells in which DNA aneuploidy has occurred.

According to an illustrative aspect of the present invention, a tumor diagnostic apparatus is provided. The tumor diagnostic apparatus includes a histogram generating section that generates a histogram from a result of a measurement of fluorescence intensity of a suspension produced from a target sample, the histogram being indicative of a relation between the fluorescence intensity and a number of cells, and a determination section that analyzes the histogram and performs a diagnosis of a tumor in the target sample. The determination section detects an S phase fluorescence intensity range corresponding to S phase cells based on the fluorescence intensity corresponding to a peak of the number of cells in the histogram, detects an abnormal fluorescence intensity range corresponding to tumor cells in which DNA aneuploidy has occurred, based on a change in the number of cells in the S phase fluorescence intensity range, and performs the diagnosis of the tumor in the target sample based on an index of the number of cells in a range defined by excluding the abnormal fluorescence intensity range from the S phase fluorescence intensity range.

DETAILED DESCRIPTION

Figure 1:
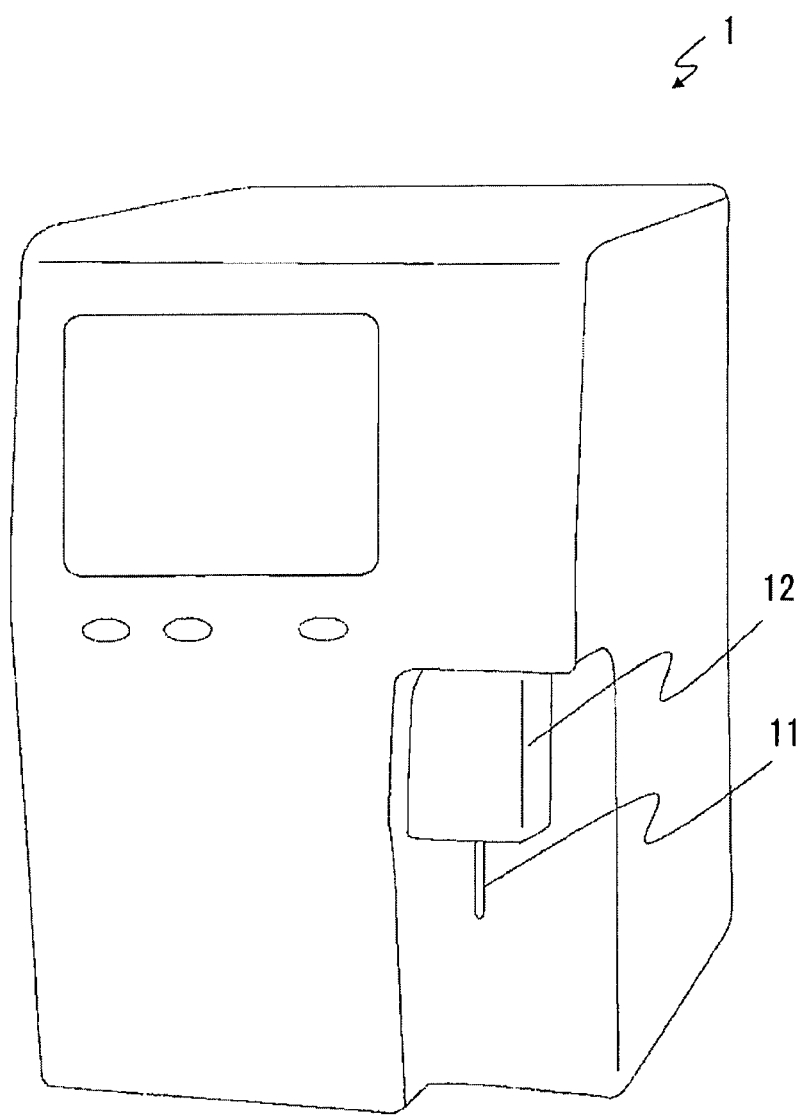
FIG. 1 is an external view of a tumor diagnostic apparatus according to an exemplary embodiment of the present invention.

An exemplary embodiment of the present invention will be described below with reference to the drawings. FIG. 1 is a perspective view illustrating an example of an external appearance of a tumor diagnostic apparatus 1 according to the exemplary embodiment. The external appearance of the tumor diagnostic apparatus 1 illustrated in FIG. 1 is merely an example, and may of course have a different form. The tumor diagnostic apparatus 1 is adapted for use in flow cytometry. In the flow cytometry, fine particles are dispersed in a fluid, the liquid (suspension) is causes to flow, and the individual particles are optically analyzed. The tumor diagnostic apparatus 1 measures the number of nucleus-stained cells in a body tissue targeted for a tumor diagnosis (hereinafter may be referred to as "target sample"), and generates a DNA histogram indicative of the relation between a number of cells and intensity of fluorescence (DNA amount)

using a result of the measurement. The tumor diagnostic apparatus 1 performs tumor analysis using the DNA histogram.

Figure 2:
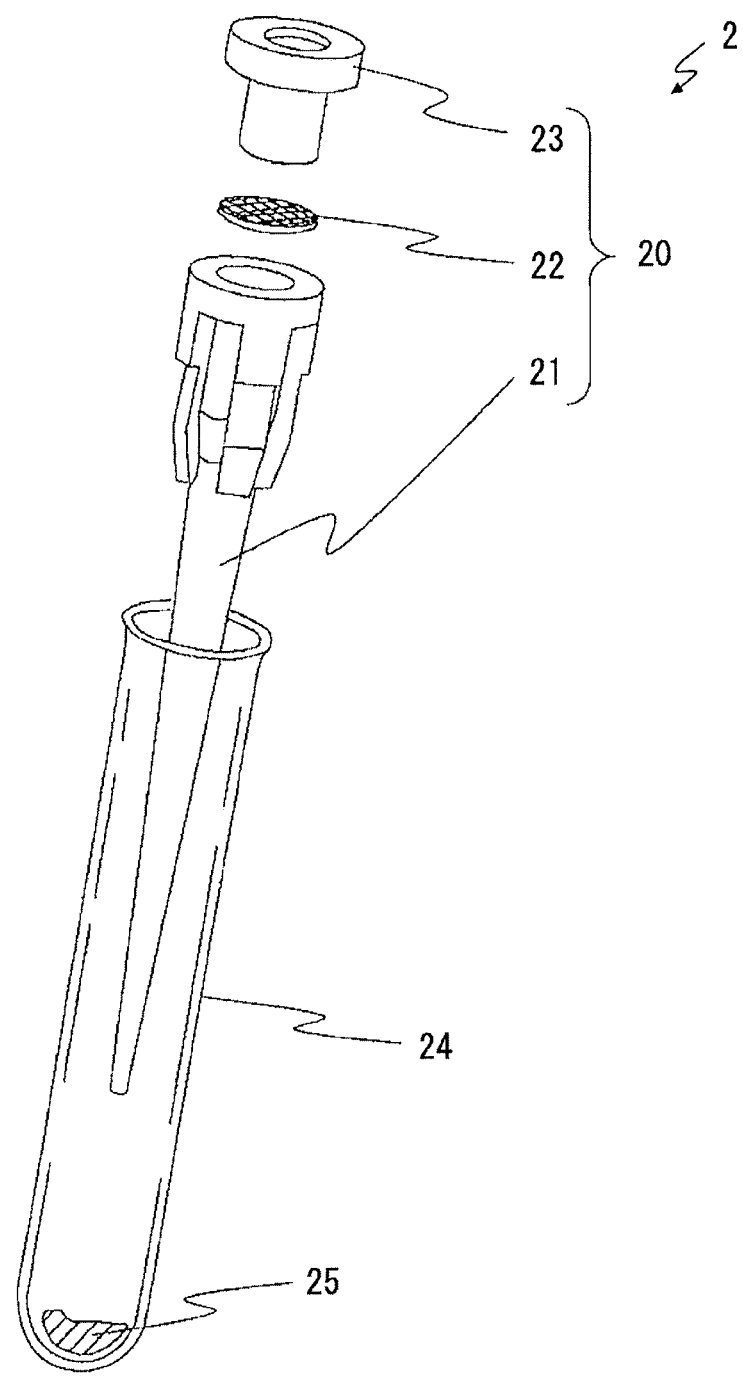
FIG. 2 is an exploded external view of a cell isolation device according to an exemplary embodiment of the present invention.

A nozzle 11 is provided in a cell pretreatment section 12 of the tumor diagnostic apparatus 1. A cell isolation device 2 is connected to the nozzle 11 to generate a suspension. FIG. 2 is an exploded external view of the cell isolation device 2. The cell isolation device 2 is provided with a pipette member 20 and a vessel 24. The pipette member 20 has a body 21, a filter 22, and a lid 23.

A reagent 25 containing a surface active agent, a ribonucleic acid (RNA) removing agent and a fluorescent dye pigment is received in the vessel 24 in a dried state or a freeze-dried state. When a biological tissue to be analyzed and a cell treatment liquid are inputted to the vessel 24, the reagent 25 is dissolved in the cell treatment liquid.

The cell isolation device 2 can make nuclei of tissue cells bare using the surface active agent, remove RNA using the RNA removing agent, and stain the bare DNA cell nuclei using a fluorescent dye pigment, in parallel with a cell isolation process using stirring as will be described later. This makes it possible to perform the measurement by the flow cytometry after being collected inside the tumor diagnostic apparatus 1.

The pipette member 20 is mounted on the vessel 24 in which the biological tissue and the cell treatment liquid (including the reagent 25) are received. A tip of the body 21 is disposed on a central axis of the vessel 24 to face a bottom of the vessel 24 with a fixed interval therebetween. The inputted biological tissue is positioned between the body 21 and the bottom of the vessel 24. The tip portion of the body 21 is soaked in the inputted cell treatment liquid.

Referring back to FIG. 1, an upper end portion (the lid 23) of the cell isolation device 2 is connected such that the nozzle 11 is inserted. A passage of the nozzle 11 and a passage inside the lid 23 communicate with each other through a suitable engagement structure. The cell pretreatment section 12 executes cell isolation process in the following procedure.

The cell pretreatment section 12 is provided with a pump mechanism (not shown) connected to the nozzle 11. The cell pretreatment section 12 controls the pump mechanism based on stirring conditions (stirring intensity, the number of times of repetition, duration, etc.) set by a user, and forms a pressurization state and a depressurization state. Air is expelled from the nozzle 11 in the pressurization state. Air is sucked into the nozzle 11 in the depressurization state.

By a pipetting process in which pressurization and depressurization are repeated, the body tissue and the cell treatment liquid (including the reagent 25) in the vessel 24 are stirred through the pipette member 20 connected to the nozzle 11. When the stirring process is performed for a fixed time, the body tissue is gradually crushed finely and minced. Thus, a suspension containing isolated cells can be obtained. In the process, membranes of the cells are broken and colored so that the DNA in the cell nuclei can react to fluorescence.

Then, the cell pretreatment section 12 sucks the suspension through the passage of the pipette member 20. The suspension is filtered through the filter 22. Thus, the suspension (cell suspended liquid) from which impurities have been removed is imported into the tumor diagnostic apparatus 1.

In the cell isolation process performed by the cell pretreatment section 12, cells may be isolated by any other method than pipetting. In addition, the suspension may be produced in advance by a technique etc. and imported into the tumor diagnostic apparatus 1.

Figure 3:
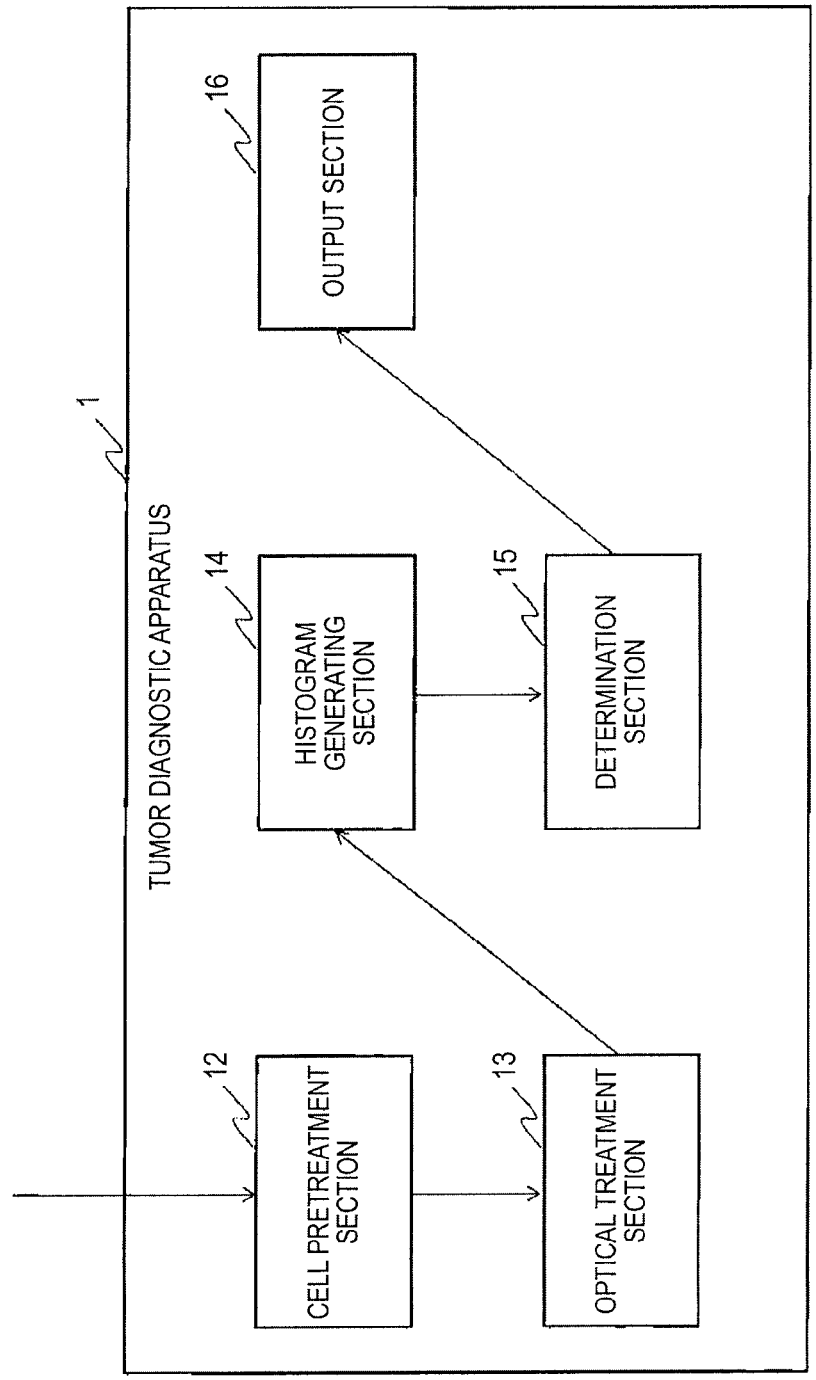
FIG. 3 is a functional block diagram of the tumor diagnostic apparatus.

Next, a process inside the tumor diagnostic apparatus 1 will be described with reference to FIG. 3. FIG. 3 is a functional block diagram of the tumor diagnostic apparatus 1. The tumor diagnostic apparatus 1 has an optical treatment section 13, a histogram generating section 14, a determination section 15, and an output section 16 in addition to the cell pretreatment section 12.

The optical treatment section 13 makes the suspension flow into a channel and irradiates the cannel with laser light. The optical treatment section 13 detects intensity of light (e.g. forward-scattered light, backward-scattered light, and lateral fluorescence) from the suspension.

The histogram generating section 14 acquires a result of the measurement of the fluorescence intensity from the optical treatment section 13. Chromosomes are made of DNA. In addition, a dye pigment is intercalated into each double-stranded DNA. Accordingly, a DNA amount can be measured based on the measurement of the intensity of the fluorescence. That is, the measurement result of the fluorescence intensity serves as data indicating a DNA amount of each cell. The histogram generating section 14 generates a DNA histogram indicative of the relation between the DNA amount (the intensity of the fluorescence) and the number of cells based on the DNA amount of each cell. The histogram generating section 14 may perform a preprocessing (e.g., flattening) before generating the histogram.

Figure 4:
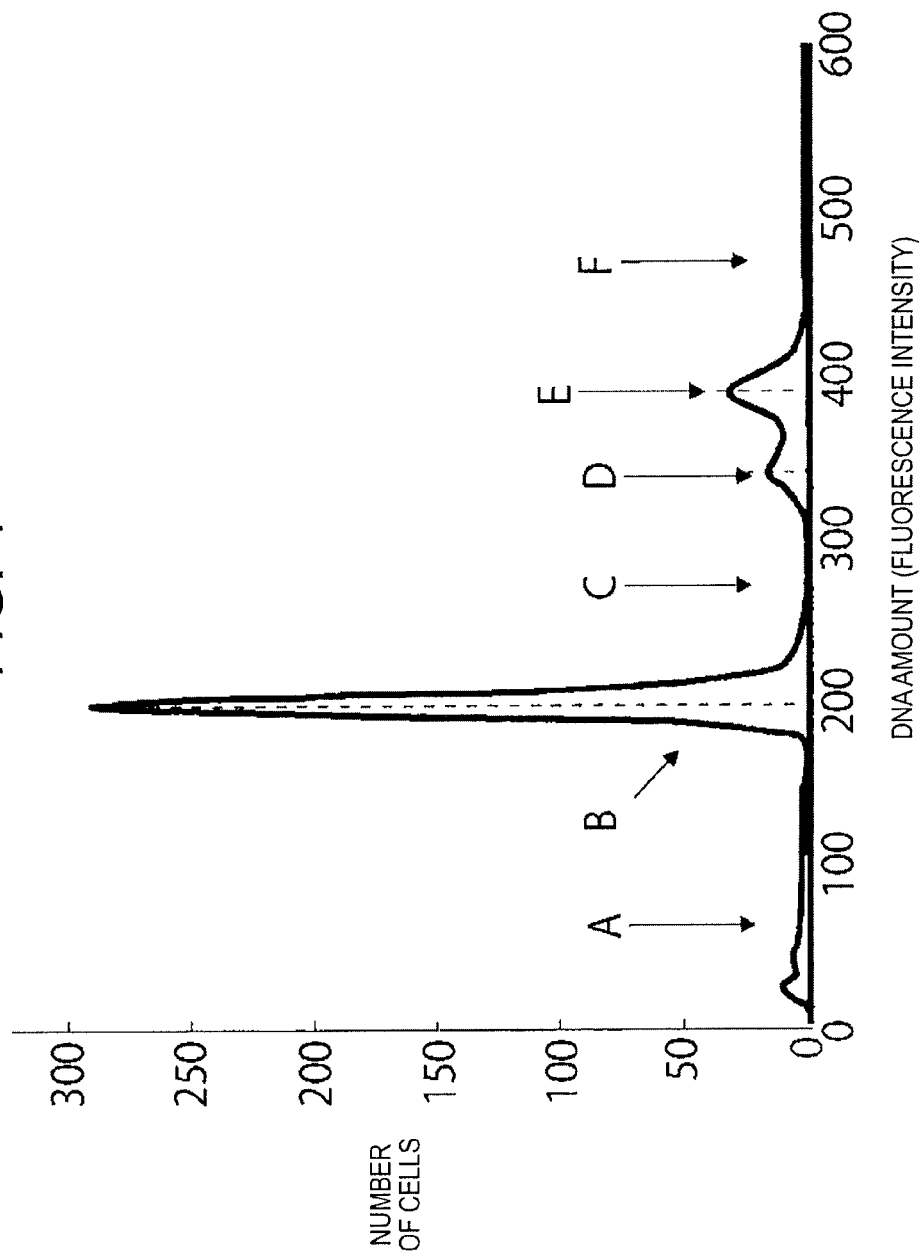
FIG. 4 is an example of a DNA histogram.

FIG. 4 illustrates an example of a DNA histogram generated by the histogram generating section 14. In FIG. 4, the region A is a region where debris, that is, destroyed cells (waste) and stromal tissues to which chromosomes are attached appear. The DNA amount in this region is smaller than the DNA amount of normal G0/G1 phase cells.

The region B is a region where a G0/G1 phase cell group, i.e., cells of normal DNA amount appears.

The region C is a region where an S phase cell group appears. In the S phase cell group, the DNA amount of cells in which DNA synthesis has just started is slightly greater than the DNA amount of the normal G0/G1 phase cells. The DNA amount continues to increase until it reaches a G2 phase level (the G2 phase corresponds to the region E which will be described below).

The region D is a region where a DNA aneuploid cell group appears. The DNA amount of cells in this region shows a distribution in an aneuploid set (not an integral multiple of the normal DNA amount). The DNA aneuploidy is often detected in a tumor tissue, and may appear in various locations. The DNA aneuploidy is not detected in a tissue where there is no tumor.

The region E is a region where a G2/M phase cell group appears. The DNA amount of the G2 phase cells is twice the DNA amount of the normal G0/G1 phase cells. The M phase cells goes through cell division in which a mother cell divides into two daughter cells. The DNA amount of the M phase cells is twice the DNA amount of the normal G0/G1 phase cells.

The region F is a region where a group of cells having other DNA amounts appears.

The DNA histogram illustrated in FIG. 4 is merely an example. The DNA histogram varies depending on a level of progress of malignant alteration in a target sample and a type of a tumor. The histogram generating section 14 provides the generated DNA histogram to the determination section 15.

The determination section 15 analyzes the DNA histogram and determines malignant alteration in the target sample. More specifically, the determination section 15 detects a range of DNA amount corresponding to the S phase cells (hereinafter may be referred to as "S phase fluorescence intensity range") in the histogram, excludes a range of DNA amount corresponding to the tumor cells (DNA aneuploidy) (hereinafter may be referred to as "abnormal fluorescence intensity range") from the S phase fluorescence intensity range, and performs a diagnosis of a type of a tumor using an index of the number of cells (e.g., a representative value of the number of cells, an AUC, and the like) in the range exclusive of the abnormal fluorescence intensity range. Detailed operation, purpose etc. of the determination section 15 will be described below.

There are various types of malignant tumors, and treatment policy differs largely from one type to another. For example, glioblastoma multiforme (GBM) is a malignant tumor that develops in a cerebrum. It is said that removing the tumor as much as possible by a craniotomy is the most effective treatment for the GBM. As another example, primary central nervous system lymphoma (PCNSL) is a malignant tumor in which lymphocytes rapidly proliferate inside the cranium. Not resection based on surgical removal but radiation therapy or chemotherapy is effective in treating the PCNSL.

Based on a detection of the DNA aneuploidy, it is possible to perform positive detection of a tumor, but it is difficult to perform a detailed diagnosis of the tumor. It has been known that malignancy of a tumor can be generally judged based on a ratio of S phase cells to all cells (see, e.g., Non-Patent Literatures 1 to 4 listed below).

Non-Patent Literature 1: Masahide Kaji et al., "Evaluation of the Predicted Proliferation Rate and Its Relation to the Tumor Marker Doubling Time in Gastric and Colorectal Cancer", The Japanese Journal of Gastroenterological Surgery, 24(10): 2493-2497, 1991

Non-Patent Literature 2: Yoshihiro Moriwaki et al., "A Clinical study on the Malignant Potential of the Remnant Gastric Cancer", The Japanese Journal of Gastroenterological Surgery, 26 (9): 2280-2286, 1993

Non-Patent Literature 3: Yutaka Yonemura and Itsuo Miyazaki, "DNA Ploidy-Usefulness and Future Outlook of Cancer Prognostic Test by Proliferative Activity Analysis", Igaku No Ayumi (Journal of Clinical and Experimental Medicine), 149: 31-34, 1989

Non-Patent Literature 4: Yutaka Yonemura, Itsuo Miyazaki et al., "DNA Ploidy Pattern, Gastric Cancer Malignancy from Perspective of Proliferative Activity", Journal of Japan Surgical Society, 89: 1175-1179, 1987

However, with a standard analysis, the ratio of the S phase cells may not be accurately obtained due to the influence of the DNA aneuploidy. This will be described with reference to FIG. 5.

Figure 5:
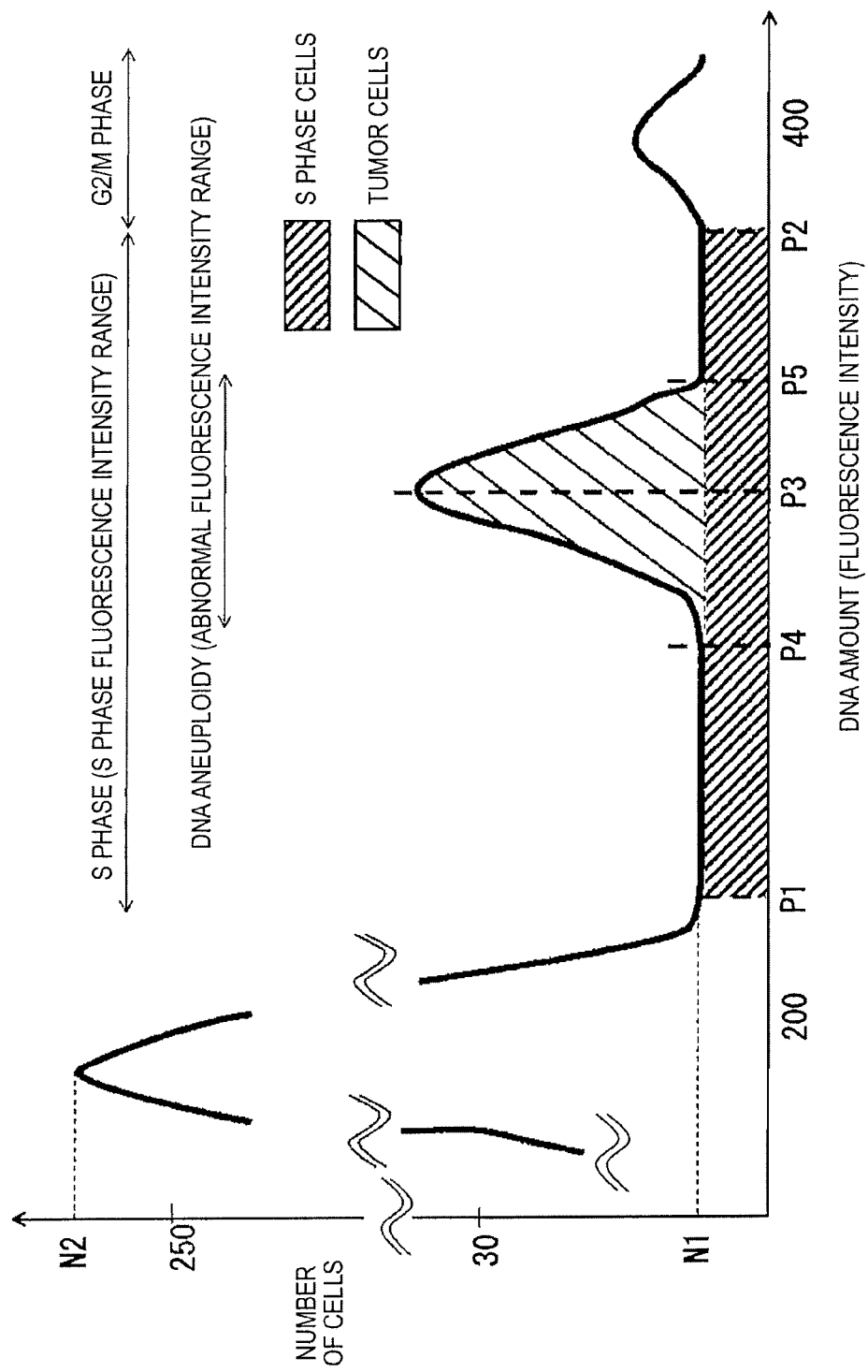
FIG. 5 is an enlarged view of an example of the DNA histogram.

FIG. 5 is an enlarged schematic view of a DNA histogram in a case where DNA aneuploidy has occurred. This DNA histogram illustrates a section of the DNA amount (intensity of fluorescence) corresponding to the S phase in an enlarged manner. In FIG. 5, a cell distribution and the like are simplified for the purpose of clear illustration.

As described above, the S phase cells are those in a transition stage from the G0/G1 phase cells to the G2/M phase cells. Here, when there are cells in which the DNA aneuploidy has occurred, these cells may have a similar DNA amount as the S phase cells. In this case, the number of the cells in which the DNA aneuploidy has occurred is added to the range of DNA amount of the S phase cells (the S phase fluorescence intensity range) and appears on the DNA histogram (the "tumor cells" portion in FIG. 5).

The determination section 15 provides means for cancelling the cell group in which the DNA aneuploidy has occurred and performing a diagnosis (as to a type or malignancy) of a tumor using an index of the number of the S phase cells (a representative value of the number of cells or an AUC) after the cancellation. Details will be described below.

First, the determination section 15 detects the range of DNA amount of the S phase cells (S phase fluorescence intensity range). As described above, the G2/M phase cells have a DNA amount that is about twice as much as that of the G0/G1 phase cells. When the DNA histogram is generated, a peak of the number of cells appears at a location corresponding to a DNA amount of the G0/G1 phase cells. Therefore, the determination section 15 sets a range of from a point near the DNA amount (the peak of amount of cells) corresponding to the G0/G1 phase cells to a point near the DNA amount of the G2/M phase cells as the range of DNA amount corresponding to the S phase cells (i.e., the S phase fluorescence intensity range). In the example of FIG. 5, the peak of the number of cells in the entire DNA histogram appears at a location corresponding to DNA amount=195. In this example, the determination section 15 sets a point of fall (P1) from the peak of the number of cells in the entire DNA histogram as a start point of the S phase fluorescence intensity range. The determination section 15 may further set a rising point (P2) of the distribution of the number of cells near the DNA amount=390 (=19×2) as an end point of the S phase fluorescence intensity range. The determination section 15 may determine, based on the peak (the DNA amount of the G0/G1 phase cells) of the DNA histogram, the start point and the end point of the S phase fluorescence intensity range in an optional way.

The determination section 15 detects a range corresponding to tumor cells in which the DNA aneuploidy has occurred (i.e., the abnormal fluorescence intensity range) within the S phase fluorescence intensity range. For example, the determination section 15 detects a peak point (P3) of the number of cells in the S phase fluorescence intensity range, and detects a rising point (P4) and a point of fall (P5) based on the peak point (P3) being a vertex therebetween. The determination section 15 sets the rising point (P4) as a start point of the abnormal fluorescence intensity range, and the fall point (P5) as an end point of the abnormal fluorescence intensity range. To identify the abnormal fluorescence intensity range, the determination section 15 may not detect the peak point (P3) of the number of cells, and instead may determine the start point and the end point of the abnormal fluorescence intensity range based on an inclination of a change of the number of cells.

The determination section 15 determines malignant alteration based on an index of the number of cells (e.g., a representative value or an AUC which will be described later in detail, indicative of a relative quantity of the S phase cells in terms of the number of cells) in a range (a range of P1 to P4 and a range of P5 to P2 in the example of FIG. 5) defined by excluding the abnormal fluorescence intensity range from the S phase fluorescence intensity range.

For example, the determination section 15 calculates a representative value of the number of cells in the range (the range of P1 to P4 and the range of P5 to P2 in the example of FIG. 5) defined by excluding the abnormal fluorescence intensity range the S phase fluorescence intensity range. The representative value may be, for example, a mean value, a mode value, or a median value of the number of cells. The determination section 15 compares the representative value (a mean N1 in the example of FIG. 5) with the peak value (a value corresponding to the number of the G0/G1 phase cells, i.e. N2 in the example of FIG. 5) of the DNA histogram. Based on the comparison, the determination section 15 can calculate a simplified ratio of the S phase cells (a ratio of the S phase cells to all the cells) from which the influence of DNA aneuploidy has been removed.

The determination section 15 compares the ratio with a predetermined threshold to evaluate a type or malignancy of a tumor. For example, in a body tissue which has a tumor caused by the GBM, the number of the S phase cells (the number of cells from which the influence of the DNA aneuploidy has been removed) is small. On the other hand, in a body tissue which has a tumor caused by the PCN SL, the number of the S phase cells (the number of cells from which the influence of the DNA aneuploidy has been removed) is greater than that in the case of the GBM. Therefore, the determination section 15 may compare the magnitude of the ratio (the simplified ratio of the S phase cells from which the influence of the DNA aneuploidy has been removed) with the threshold to evaluate the type of the tumor. In addition, it has been known that each pattern of the DNA histogram reflects the malignancy of tumor cells, and there is therefore a significant relation between the ratio of the S phase cells (proliferating cells) and the malignancy of the tumor (see, e.g., the previously listed Non-Patent Literatures 1 to 4). Therefore, the determination section 15 may, for example, compare the ratio of the S phase cells with the predetermined threshold to thereby evaluate the malignancy (malignant level) of the tumor.

The determination section 15 may compare an area under the curve (AUC) in the range (the range of P1 to P4 and the range of P5 to P2 in the example of FIG. 5) defined by excluding the abnormal fluorescence intensity range from the S phase fluorescence intensity range, with an AUC in the entire range. The DNA histogram indicates a distribution of the number of cells for each DNA amount. Thus, the AUC corresponds to a total value of the number of cells in a certain range. By the comparison, the determination section 15 can calculate the ratio of the S phase cells (the ratio of the S phase cells to all the cells) from which the influence of the DNA aneuploidy has been removed. The determination section 15 may compare the ratio with a predetermined threshold to evaluate a type of a tumor. In addition, the determination section 15 may use the ratio to evaluate malignancy of the tumor.

The determination section 15 may perform the comparison with a range (the regions B to F) defined by excluding a range (the region A) corresponding to debris from the entire range (the regions A to F in FIG. 4). In this way, the determination section 15 can remove the influence of the debris in calculating the ratio of the S phase cells, and so that a type or malignancy of a tumor can be determined more accurately.

As described above, the determination section 15 identifies a range (the range of P1 to P4 and the range of P5 to P2 in the example of FIG. 5) defined by excluding the abnormal fluorescence intensity range from the S phase fluorescence intensity range, and determines a type or malignancy of a tumor based on the magnitude of an index value (the representative value, the AUC, or the like) indicative of the number of cells in the range.

Figure 6:
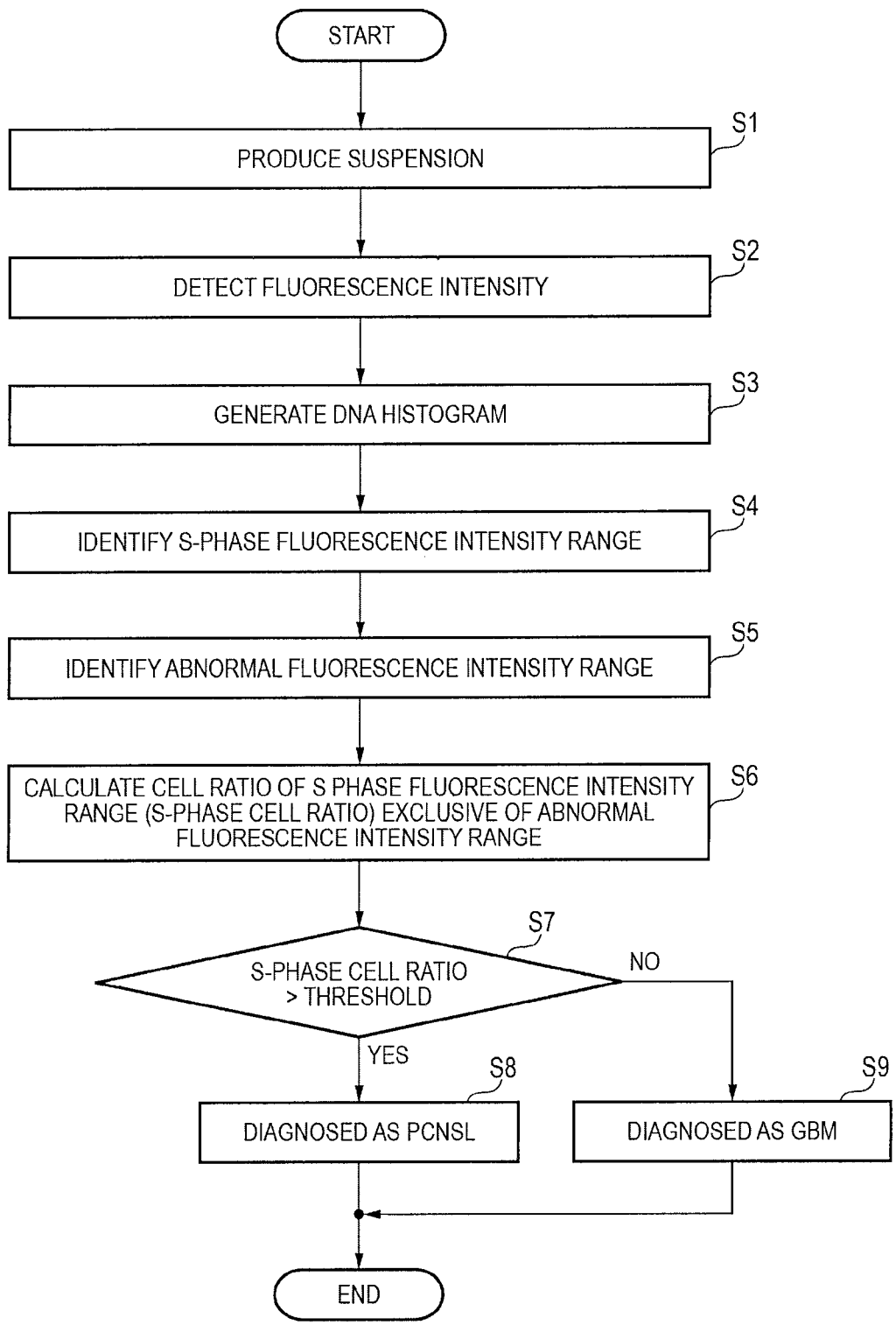
FIG. 6 is a flow chart illustrating a flow of a process to be carried out with the tumor diagnostic apparatus.

Referring back to FIG. 3, the output section 16 outputs a result of the tumor diagnosis. The way of output is optional. For example, the output section 16 may display the result of the tumor diagnosis on a display provided on a housing of the tumor diagnostic apparatus 1. The output section 16 may notify a user of the tumor, such as the type of the tumor, in the target sample in an audible manner Next, operations of the tumor diagnostic apparatus 1 will be described again with reference to FIG. 6. FIG. 6 is a flow chart illustrating a flow of operations to be performed by the tumor diagnostic apparatus 1 to determine a type of a tumor. This example shows a processing flow for discriminating the GBM and the PCNSL from each other. Though not mentioned in FIG. 6, an equivalent process can be performed to determine malignancy of the tumor.

The cell pretreatment section 12 performs cell isolation by a pipetting process on a target sample, and generates a suspension in which cells have been stained with a fluorescent dye pigment (S1). The cell pretreatment section 12 may perform cell isolation by another method. In addition, a suspension which has been produced in advance may be fed to the tumor diagnostic apparatus 1.

The optical treatment section 13 applies laser light to the suspension made to flow in a channel, and detects intensity of light (including lateral fluorescence) from the suspension (S2). The histogram generating section 14 generates a DNA histogram indicative of the relation between a DNA amount (the intensity of the fluorescence) and a number of cells based on a result of a measurement of the fluorescence intensity detected by the optical treatment section 13 (S3).

The determination section 15 detects the DNA amount (the intensity of the fluorescence) corresponding to G0/G1 phase cells from the DNA histogram, and detects a range of DNA amount corresponding to S phase cells (S phase fluorescence intensity range) based on the detected DNA amount (S4). Then, the determination section 15 detects a range corresponding to tumor cells (abnormal fluorescence intensity range) in which DNA aneuploidy has occurred within the S phase fluorescence intensity range (S5).

The determination section 15 calculates a ratio of a mean value (an example of the index) of the number of cells in the range defined by excluding the abnormal fluorescence intensity range from the S phase cell fluorescence intensity range, with the number of the G0/G1 phase cells (a peak value of the histogram) (S6). The determination section 15 may perform the comparison using the AUC or the like in the range, as described above.

The determination section 15 compares the calculated ratio (the S phase cell ratio) with a predetermined threshold (S7). When the S phase cell ratio is greater than the predetermined threshold (S7:YES), the determination section 15 determines that the target sample is suspected to be PCNSL (S8). On the other hand, when the S phase cell ratio is not greater than the predetermined threshold (S7:NO), the determination section 15 determines that the target sample is suspected to be GBM (S9). The predetermined threshold used for the comparison may be determined based on experience of pathological diagnosis.

The determination section 15 may compare the S phase cell ratio with a plurality of thresholds to discriminate three tumor types or more from one another. In addition, the determination section 15 may determine various tumor types such as gastric cancer and colorectal cancer using the ratio described above (the S phase cell ratio).

Next, advantageous effects of the tumor diagnostic apparatus 1 according to the exemplary embodiment will be described. As described above, previously, there has been a problem that the number of the S phase cells cannot be obtained accurately due to the influence of the cells in which the DNA aneuploidy has occurred.

According to the exemplary embodiment, the determination section 15 detects, in the DNA histogram, the range of the S phase cells exclusive of the range corresponding to the DNA aneuploidy (e.g., the range of P1 to P4 and the range of P5 to P2 in FIG. 5). The determination section 15 performs the diagnosis of the tumor, e.g., determines a type of a tumor, using the index of the number of cells in the detected range. By removing the influence of the DNA aneuploidy, the determination section 15 can accurately perform the diagnosis such as determining the type or malignancy of the tumor.

The determination section 15 calculates a representative value of the range of the S phase cells (e.g. the range of P1 to P4 and the range of P5 to P2 in FIG. 5) in which the range corresponding to the DNA aneuploidy has been excluded from the DNA histogram. The determination section 15 can compare the representative value (preferably the mean, i.e. N1 in the example of FIG. 5) with the peak value (the number of cells corresponding to the G0/G1 phase cells, i.e. N2 in the example of FIG. 5) of the DNA histogram so that an index (ratio) of the number of the S phase cells relative to all cells can be grasped simply and accurately. The determination section 15 can use the ratio to determine the type or malignancy of the tumor simply and accurately.

In addition, the determination section 15 may compare an AUC of the range of the S phase cells (e.g. the range of P1 to P4 and the range of P5 to P2 in the example of FIG. 5) in which the range corresponding to the DNA aneuploidy has been excluded from the DNA histogram, with an AUC of the entire DNA histogram. Even in this case, the determination section 15 can merely perform general statistical processing to calculate an index of a ratio of normal S phase cells to all the cells. Accordingly, the determination section 15 can determine a type or malignancy of a tumor easily and accurately.

While the present invention has been described with reference to a certain exemplary embodiment thereof, the scope of the present invention is not limited to the exemplary embodiment described above, and it will be understood by those skilled in the art that various changes and modifications may be made therein without departing from the scope of the present invention as defined by the appended claims For example, the determination section 15 may also perform various kinds of detection of malignant alteration using the DNA histogram. Specifically, the determination section 15 may detect malignant alteration of the target sample based on general detection of the DNA aneuploidy. In addition, the determination section 15 may perform analysis described in JP2014-23439A.

A portion of the processing of the optical treatment section 13, the processing of the histogram generating section 14 and the processing of the determination section 15 may be achieved by execution of a program which is read by a central processing unit (CPU, not shown) from a storage portion (e.g. a hard disk in the tumor diagnostic apparatus 1). The CPU is provided in the tumor diagnostic apparatus 1.

The program can be stored in various types of non-transitory computer-readable medium and supplied to a computer. The non-transitory computer-readable medium include various types of tangible storage medium. Examples of the non-transitory computer-readable medium include magnetic recording media (such as a flexible disk, a magnetic tape, and a hard disk drive), magneto-optical recording media (such as a magneto-optical disk), CD-read only memory (CD-ROM), CD-R, CD-R/W, and semiconductor memories (such as a mask ROM, a programmable ROM (PROM), an erasable PROM (EPROM), a flash ROM, and an random access memory (RAM)). The program may be supplied to the computer by any of various types of transitory computer-readable media. Examples of the transitory computer-readable media include electrical signals, optical signals and electromagnetic waves. The transitory computer-readable media can supply the program to the computer through wired communication channels such as an electric cable and an optical fiber or through wireless communication channels.

The invention claimed is:

1. A tumor diagnostic apparatus comprising:
   a non-transitory computer readable medium storing a program;
   and a processor configured to execute the program including the following the steps:
   generating a histogram from a result of a measurement of fluorescence intensity of a suspension, the suspension having been produced from a target sample and comprising a cell containing DNA that is fluorescently stained, the histogram being indicative of a relation between the fluorescence intensity and a number of cells; and
   analyzing the histogram and performing a diagnosis of a tumor in the target sample,
   wherein the performing the diagnosis comprises:
   detecting an S phase fluorescence intensity range corresponding to S phase cells based on the fluorescence intensity corresponding to a peak of the number of cells in the histogram,
   detecting an abnormal fluorescence intensity range corresponding to tumor cells in which DNA aneuploidy has occurred, based on a change in the number of cells in the S phase fluorescence intensity range, and
   performing the diagnosis of the tumor in the target sample based on an index of the number of cells in a modified range defined by excluding the abnormal fluorescence intensity range from the S phase fluorescence intensity range.

2. The tumor diagnostic apparatus according to claim 1, wherein the diagnosis of the tumor is a determination of a type of the tumor or a determination of malignancy of the tumor.

3. The tumor diagnostic apparatus according to claim 1, wherein analyzing the histogram compares a representative value of the number of cells in the modified range with a value of the peak in the histogram to perform the diagnosis of the tumor in the target sample.

4. The tumor diagnostic apparatus according to claim 3, wherein the representative value is a mean value, a mode value, or a median value.

5. The tumor diagnostic apparatus according to claim 1, wherein the determination section compares an area under a curve in the modified range with an area under a curve in an entire range of the histogram to perform the diagnosis of the tumor in the target sample.

6. The tumor diagnostic apparatus according to claim 1, wherein the determination section compares an area under a curve in the modified range with an area under a curve in a range defined by excluding a range corresponding to debris from an entire range of the histogram to perform the diagnosis of the tumor in the target sample.

7. A tumor diagnostic method comprising:
   generating a histogram from a result of a measurement of fluorescence intensity of a suspension, the suspension having been produced from a target sample and comprising a cell containing DNA that is fluorescently stained, the histogram being indicative of a relation between the fluorescence intensity and a number of cells; and
   performing a diagnosis of a tumor in the target sample by analyzing the histogram,
   wherein the performing the diagnosis comprises:

detecting an S phase fluorescence intensity range corresponding to S phase cells based on the fluorescence intensity corresponding to a peak of the number of cells in the histogram;

detecting an abnormal fluorescence intensity range corresponding to tumor cells in which DNA aneuploidy has occurred, based on a change in the number of cells in the S phase fluorescence intensity range; and performing the diagnosis of the tumor in the target sample based on an index of the number of cells in a range defined by excluding the abnormal fluorescence intensity range from the S phase fluorescence intensity range.

8. A non-transitory computer readable medium storing a program which, when executing on a computer, causes the computer to execute a method comprising:

generating a histogram from a result of a measurement of fluorescence intensity of a suspension, the suspension having been produced from a target sample and comprising a cell containing DNA that is fluorescently stained, the histogram being indicative of a relation between the fluorescence intensity and a number of cells; and performing a diagnosis of a tumor in the target sample by analyzing the histogram, wherein the performing the diagnosis comprises:

detecting an S phase fluorescence intensity range corresponding to S phase cells based on the fluorescence intensity corresponding to a peak of the number of cells in the histogram;

detecting an abnormal fluorescence intensity range corresponding to tumor cells in which DNA aneuploidy has occurred, based on a change in the number of cells in the S phase fluorescence intensity range; and performing the diagnosis of the tumor in the target sample based on an index of the number of cells in a range defined by excluding the abnormal fluorescence intensity range from the S phase fluorescence intensity range.

* * * * *

UNITED STATES PATENT AND TRADEMARK OFFICE
CERTIFICATE OF CORRECTION

PATENT NO. : 10,633,709 B2
APPLICATION NO. : 15/491327
DATED : April 28, 2020
INVENTOR(S) : Takahiro Shioyama et al.

Page 1 of 1

It is certified that error appears in the above-identified patent and that said Letters Patent is hereby corrected as shown below:

In the Specification

Column 6, Line 25, "amount=390 (=19×2) as an" should read -- amount=390 (=195×2) as an --

Signed and Sealed this
Fifteenth Day of September, 2020

Andrei Iancu
*Director of the United States Patent and Trademark Office*